United States Patent [19]

Illig

[11] Patent Number: 5,330,739

[45] Date of Patent: Jul. 19, 1994

[54] IODINATED BENZOYL ACETALS AND KETALS FOR X-RAY IMAGING

[75] Inventor: Carl R. Illig, Phoenixville, Pa.

[73] Assignee: Sterling Winthrop Inc., New York, N.Y.

[21] Appl. No.: 985,415

[22] Filed: Dec. 4, 1992

[51] Int. Cl.$^5$ ............... A61K 49/04; C07C 205/00; C07C 229/00; C07C 69/76
[52] U.S. Cl. .................. 424/5; 560/22; 560/47; 560/60; 560/65; 560/83
[58] Field of Search ............. 424/5; 560/22, 60, 65, 560/83, 47

[56] References Cited

U.S. PATENT DOCUMENTS

| | | | |
|---|---|---|---|
| 3,795,698 | 3/1974 | Soulal et al. | 560/37 |
| 4,018,783 | 4/1977 | Soulal et al. | 260/343.3 X |
| 4,225,725 | 9/1980 | Hoey | 560/37 |
| 4,567,034 | 1/1986 | Charles et al. | 424/5 |

FOREIGN PATENT DOCUMENTS 0300828  1/1989  European Pat. Off. .

*Primary Examiner*—Gary E. Hollinden
*Attorney, Agent, or Firm*—William J. Davis

[57] ABSTRACT

Compounds having the structure $$(Z)\!-\!\underset{\underset{}{\|}}{C}\!-\!O\!-\!\underset{\underset{R^2}{|}}{\overset{\overset{OR}{|}}{C}}\!-\!R^1$$
$$\phantom{(Z)\!-\!C\!-\!}O$$

wherein (Z)–COO is the residue of an iodinated aromatic acid;

R is alkyl, cycloalkyl, aryl, aralkyl, $$-\underset{\|}{\overset{O}{C}}\text{-alkyl}, -\underset{\|}{\overset{O}{C}}\text{-aryl},$$

or alkenyl;

$R^1$ is H, alkyl, cycloalkyl, aryl, aralkyl, or $-(CH_2)_m$-$CO_2R^3$;

$R^2$ is H, alkyl, cycloalkyl, aryl, aralkyl, $-(CH_2)_n$-$CO_2R^4$, or a $$-(CH_2)_p\underset{\underset{R^1}{|}}{\overset{\overset{OR}{|}}{C}}-O-\underset{\|}{\overset{O}{C}}-(Z)$$

group, wherein Z, R and $R^1$ are as defined above;
or $R^1$ and $R^2$, taken together with the carbon atom to which they are attached represent cycloalkyl;
$R^3$ is H, alkyl, cycloalkyl, aryl or aralkyl;
$R^4$ is H, alkyl, cycloalkyl, aryl or aralkyl; and
m, n and p are independently an integer of from 0 to 17;
provided that $R^1$ and $R^2$ can not both be H;

are useful in the preparation of x-ray contrast compositions for medical imaging.

7 Claims, No Drawings

IODINATED BENZOYL ACETALS AND KETALS FOR X-RAY IMAGING

FIELD OF INVENTION

This invention relates to iodinated benzoyl acetals and ketals which are particularly useful as contrast agents for x-ray imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, *Pharmaceuticals in Medical Imaging,* 1990, MacMillan Publishing Company.

The following references describe various iodine containing compounds useful in preparing x-ray contrast compositions.

U.S. Pat. No. 3,097,228 describes derivatives of 2,4,6-triiodobenzoyloxyalkanoic acids having the structure

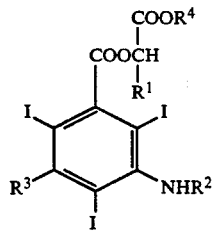

wherein $R^1$ is H or lower alkyl; $R^2$ is H or lower-alkanoyl; and $R^3$ is H or lower alkanoylamino and $R^4$ is lower alkyl. However, there is no suggestion of benzoyl acetals or ketals.

U.S. Pat. No. 3,144,479 describes iodinated benzoic acid esters having the formula

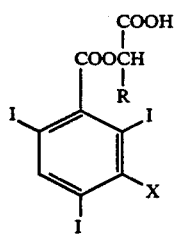

wherein X is an iodine atom or an amino group and R is selected from H, alkyl, alkoxyalkyl, i.e., $-(CH_2)_m-O-R''$, wherein $R''$ is alkyl and m is 1 or 2, phenyl and a particular iodinated aromatic group. However, there is no suggestion of benzoyl acetals or ketals.

U.S. Pat. No. 4,567,034 discloses esters of diatrizoic acid as x-ray contrast agents having the structure

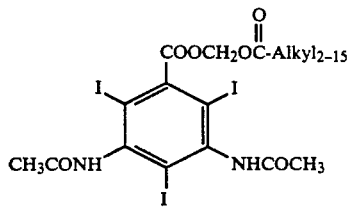

However, these agents, upon hydrolysis, can release formaldehyde which is undesirable.

PCT/EP90/00053 describes iodine containing carbonate esters having the structure

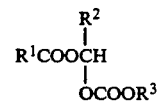

wherein $R^1$ and $R^3$ are an aliphatic, araliphatic, aryl or heterocyclic group; and $R^2$ is H, aliphatic, aryl, or araliphatic for use as particulate x-ray contrast agents.

EP-A 498,482 describes nanoparticulate x-ray contrast compositions which have proven to be extremely useful in medical imaging. However, contrast agents comprised of iodinated esters, such as WIN 8883, i.e., the ethyl ester of diatrizoic acid, in some in vivo applications and for reasons that are not completely understood can exhibit less than fully satisfactory hydrolysis and/or metabolic profiles.

It would be desirable to provide compounds for use as x-ray contrast agents having improved hydrolysis and/or metabolic profiles.

SUMMARY OF THE INVENTION

I have discovered and prepared novel iodinated aromatic benzoyl acetals and ketals which are useful in the preparation of x-ray contrast compositions.

More specifically, in accordance with this invention, there are provided compounds having the structure I $$(Z)\!\!-\!\!\overset{O}{\underset{}{C}}\!\!-\!\!O\!\!-\!\!\overset{OR}{\underset{R^2}{C}}\!\!-\!\!R^1 \qquad (I)$$

wherein $(Z)\!\!-\!\!COO$ is the residue of an iodinated aromatic acid;

R is alkyl, cycloalkyl, aryl, aralkyl,

or alkenyl;

$R^1$ is H, alkyl, cycloalkyl, aryl, aralkyl, or $-(CH_2)_m-CO_2R^3$;

$R^2$ is H, alkyl, cycloalkyl, aryl, aralkyl, $-(CH_2)_n-CO_2R^4$, or a

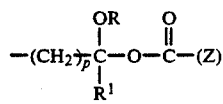

group, wherein Z, R and R¹ are as defined above;
or R¹ and R² taken together with the carbon atom to which they are attached represent cycloalkyl;

R³ is H, alkyl, cycloalkyl, aryl or aralkyl;

R⁴ is H, alkyl, cycloalkyl, aryl or aralkyl; and m, n and p are independently an integer of from 0 to 17;
provided that R¹ and R² can not both be H.

This invention further provides an x-ray contrast composition comprising the above-described compound and a method for medical x-ray diagnostic imaging which comprises administering to the body of a test subject an effective contrast producing amount of the above-described x-ray contrast composition.

It is an advantageous feature of this invention that novel compounds are provided which find particular utility as x-ray contrast agents.

It is another advantageous feature of this invention that compounds are provided which hydrolyze to an iodinated benzoate (known to be relatively safe) that is rapidly excreted from the body, and to biologically acceptable alcohols and/or acids and a carbonyl compound which are excretable or metabolizable and relatively nontoxic.

DESCRIPTION OF PREFERRED EMBODIMENTS

In structural formula I above, (Z—COO is the residue of an iodinated acid. The acid can be aromatic or nonaromatic. Aromatic acids are preferred when used in vivo for safety. The iodinated acid can comprise one, two, three or more iodine atoms per molecule. Preferred species contain at least two, and more preferably, at least three iodine atoms per molecule. The iodinated compounds can contain substituents which do not deleteriously effect the contrast enhancing capability of the compound.

Illustrative examples of suitable aromatic acids include
diatrizoic acid,
metrizoic acid,
iothalamic acid,
trimesic acid,
ioxaglic acid (hexabrix),
ioxitalamic acid, tetraiodoterephthalic acid,
iodipamide, and the like. In the compound of this invention, one or more of the carboxyl groups of the aromatic acid selected is functionalized as in structure I. In preferred embodiments, (Z—)—COO is the residue of a substituted triiodobenzoic acid such as an acylamino and/or carbamyl substituted triiodobenzoic acid.

R represents H, a substituted or unsubstituted linear or branched alkyl group; preferably containing from 1 to 20, more preferably, 2 to 8 carbon atoms, such as ethyl, propyl, isopropyl, butyl, isobutyl, sec-butyl, pentyl, hexyl and the like; cycloalkyl, preferably containing from 3 to 8 carbon atoms, such as cyclopentyl and cyclohexyl; aryl, preferably containing from 6 to 10 carbon atoms, such as phenyl and naphthyl;

the alkyl portion of which is described for R above
aralkyl, preferably containing from 7 to 12 carbon atoms, such as benzyl;

the aryl portion of which is described for R above; or alkenyl, preferably containing from 2 to 8 carbon atoms such as ethenyl and propenyl.

R¹ can be H; alkyl, preferably containing from 1 to 20 carbon atoms such as described for R above; cycloalkyl, preferably containing from 3 to 8 carbon atoms, such as cyclopentyl and cyclohexyl; aryl, preferably containing from 6 to 10 carbon atoms, such as phenyl and naphthyl; aralkyl, such as benzyl; or $-(CH_2)_m CO_2 R^3$, wherein m is an integer from 0 to 17, and R³ is H, alkyl, cycloalkyl, aryl or aralkyl as described for R¹ above.

R² can be H, alkyl, preferably containing from 1 to 20 carbon atoms such as described for R above; cycloalkyl, preferably containing from 3 to 8 carbon atoms such as cyclopropyl and cyclobutyl; aryl, preferably containing from 6 to 10 carbon atoms such as phenyl and naphthyl; aralkyl, preferably containing from 7 to 12 carbon atoms such as benzyl; $-(CH_2)_n CO_2 R^4$, wherein n is an integer from 0 to 17, and R⁴ is H, alkyl, cycloalkyl, aryl or aralkyl as described for R¹ above; or a

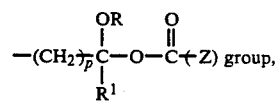

wherein Z, R and R¹ are as defined above and p is an integer from 0 to 17.

R¹ and R², taken together with the carbon atom to which they are attached, can represent cycloalkyl, preferably containing from 3 to 8 carbon atoms, such as cyclopropyl, cyclobutyl, cyclopentyl, and the like. As noted, R¹ and R² can not both be H.

R³ can be H; alkyl, preferably containing from 1 to 20 carbon atoms, and more preferably from 2 to 8 carbon atoms, such as described for R¹; cycloalkyl preferably containing from 3 to 8 carbon atoms such as cyclopentyl and cyclohexyl; aryl, preferably containing from 6 to 10 carbon atoms, such as phenyl and naphthyl; or aralkyl, preferably containing from 7 to 12 carbon atoms, such as benzyl.

R⁴ can be H, alkyl, preferably containing from 1 to 20 carbon atoms, more preferably from 2 to 8 carbon atoms, such as described for R¹; cycloalkyl, preferably containing from 3 to 8 carbon atoms such as cyclopentyl and cyclohexyl; aryl, preferably containing from 6 to 10 carbon atoms, such as phenyl and naphthyl; or aralkyl, preferably containing from 7 to 12 carbon atoms, such as benzyl.

The alkyl, cycloalkyl, aryl, aralkyl and alkenyl groups in structure I above can be unsubstituted or substituted with various substituents which do not adversely affect the efficacy of the compounds as x-ray contrast agents such as alkyl, cycloalkyl, aryl, aralkyl, hydroxy, lower alkoxy, acyloxy, halogen, such as chlorine and iodine, acylamino, carboalkoxy, carbamyl and the like.

The compounds of this invention can be prepared by alkylation of the carboxylate of an iodinated aromatic acid with an alkoxy derivative having the formula

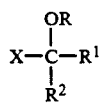

wherein X is a leaving group and R, $R^1$ and $R^2$ are as defined above. Suitable leaving groups include halogen such as Br, I and Cl; and sulfonyloxy, such as methanesulfonyloxy and toluenesulfonyloxy. The carboxylates of iodinated aromatic acids and the alkoxy derivatives useful as starting materials in the preparation of the compounds of the invention are known compounds and/or can be prepared by techniques well known in the art. A general reaction scheme for the displacement reaction is as follows:

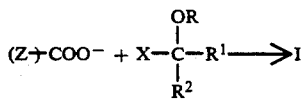

The reaction can take place at temperatures ranging from −b 78° C. to 100° C., more preferably −40° C. to 50° C. For convenience, the reaction can take place at atmospheric pressure, however, higher and lower pressures are contemplated.

The solvent for the reaction can be any which does not adversely react with the starting materials or product. Suitable solvents include N,N-dimethylformamide.

When used as an x-ray contrast agent, the compound of this invention preferably comprises at least about 35%, more preferably at least 40% iodine by weight.

In preferred embodiments, the compounds of this invention can be formulated into particulate x-ray contrast compositions, preferably nanoparticulate x-ray contrast compositions, as described in commonly-owned EPO 498,482, the disclosure of which is hereby incorporated by reference in its entirety. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition.

The x-ray contrast compositions of this invention comprise the above-described compounds, preferably in the form of particles, and a carrier therefor. For example, the particles can be dispersed in an aqueous liquid which serves as the carrier for the x-ray contrast agent. Other suitable carriers include liquid carriers such as mixed aqueous and nonaqueous solvents, for example water and alcohols, and suitable nonaqueous solvents, such as alcohol; gels; gases, such as air; and powders.

The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anticlotting agents, mixing agents, and other drugs and the like can be added. A partial listing of certain specific additives includes gums, sugars such as dextran, human serum albumin, gelatin, sodium alginate, agar, dextrin, pectin and sodium carboxymethylcellulose. Such additives, surface active agents, preservatives and the like can be incorporated into the compositions of the invention.

A method for diagnostic imaging for use in medical procedures in accordance with this invention comprises administering to the body of a test subject in need of an x-ray examination an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of the tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool, liver, spleen and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Preparation of Ethyl 2-diatrizoxy-2-ethoxyacetate (WIN 65619)

To a flame-dried 1 L flask containing 2.05 g (85.5 mmol) sodium hydride (dry powder, Aldrich) under nitrogen was added 450 mL dry N, N-dimethylformamide (DMF). 50.0 g (81.4 mmol) diatrizoic acid was added in 5 portions over 10 min with stirring. Significant gas evolution was observed. The mixture was stirred for 15 minutes at room temperature to yield a pale yellow clear solution. Ethyl 2-bromo-2-ethoxyacetate (24.1 g, 114 mmol, prepared from ethyl 2-ethoxyacetate according to the method of Carpino, *J. Org. Chem.*, 29, 2820 (1964)) in 50 mL dry DMF was added dropwise from an addition funnel over 10 min. After 40 min, TLC (20% $CH_3OH-CH_2Cl_2$ taken on a 1 ml aliquot quenched in 4 ml of water, filtered and air-dried) indicated no remaining acid and a new high-$R_f$ product present.

After 2 h total time from addition of the bromide, the clear, pale yellow solution was poured into 2200 mL distilled water containing 2.74 g (32.6 mmol) $NaHCO_3$ with vigorous stirring. A clear solution resulted which began to precipitate a white solid within 30 sec. The mixture was stirred at room temperature for 15 min, then cooled in ice water with stirring to about 15° C. The mixture was filtered and the white solid was washed with three 50 mL aliquots of water. The product was air-dried under suction 1.5 h, then over $P_2O_5$ (40° C./2 torr/18 hr) to afford 3.72 g of a white powder (62%) having structure I above, wherein (Z─)─COO═ the residue of diatrizoic acid, R═$CH_2CH_3$, $R^1$═H and $R^2$═$COOCH_2CH_3$ (WIN 65619). $^1H$ and $^{13}C$ NMR and mass spectroscopic analysis were consistent with the desired mixed glyoxylate acetal. mp 265°–267° C. (decomp.)

Elemental analysis

Calc'd for $C_{17}H_{19}I_3N_2O_7$: C) 27.44 H) 2.57 N) 3.76 I) 51.17; Found: C) 27.44 H) 2.59 N) 3.73 I) 51.27.

This compound provides good imaging as a particle for the blood, liver, spleen, and lymph nodes. In addition, it provides good clearance due to its metabolic breakdown into ethanol, glyoxylic acid and diatrizoic acid.

EXAMPLE 2

Preparation of ethyl 2-diatrizoxy-2-n-hexyloxyacetate

The title product was prepared in a similar manner to Example 1. Thus, ethyl n-hexyloxyacetate (prepared using the methodology of H. Gershon, et al, *J. Pharm. Sci.*, 68, 82 (1979)) was converted to ethyl 2-bromo-2-n-hexyloxyacetate, again using the procedure of Carpino, *J. Org. Chem.*, 29, 2820 (1964). Reaction of this bromide with sodium diatrizoate in DMF, as described above, afforded a white powder in 53% yield, mp 217°–219° C., having the structure I wherein (Z─)─COO═the residue of diatrizoic acid, R═$(CH_2)_5CH_3$, $R^1$═H, and $R^2$═$CO_2CH_2CH_3$. $^1H$ and $^{13}C$ NMR spectroscopic analysis were consistent with the desired product.

The invention has been described in detail with particular reference to certain preferred embodiments thereof, but it will be understood that variations and modifications can be effected within the spirit and scope of the invention.

What is claimed is:

1. A compound having the structure

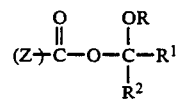

wherein (Z─)─COO is the residue of an iodinated aromatic acid; R is alkyl, cycloalkyl, aryl, aralkyl,

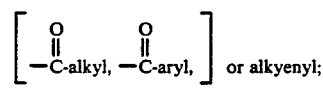

or alkyenyl;

$R^1$ is H, alkyl cycloalkyl, aryl, aralkyl, or ─(─$CH_2$─)$_m$─$CO_2R^3$;

$R^2$ is ─(─$CH_2$─)$_n$$CO_2R^4$, or a

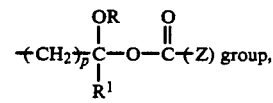

group, wherein

Z, R and $R^1$ are as defined above; or $R^1$ and $R^2$, taken together with the carbon atom to which they are attached represent cycloalkyl;

$R^3$ is H, alkyl, cycloalkyl, aryl or aralkyl;

$R^4$ is H, alkyl, cycloalkyl, aryl or aralkyl; and m, n and p are independently an integer of from 0 to 17.

2. The compound of claim 1 wherein (Z─)─COO is the residue of an iodinated aromatic acid selected from:

diatrizoic acid, metrizoic acid, iothalamic acid, trimesic acid, ioxagalic acid, ioxitalamic acid, tetraiodoterephthalic acid and iodipamide.

3. The compound of claim 1 wherein (Z─)─COO is the residue of diatrizoic acid.

4. The compound of claim 1 wherein R is alkyl, $R^1$ is H, $R^2$ is ─$CO_2R^3$, and $R^3$ is alkyl.

5. The compound of claim 1 having the structure

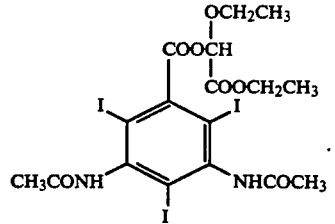

6. An X-ray contrast composition comprising the compound of claim 1 in the form of particles, a surface modifier for said particles, and a pharmaceutically acceptable carrier.

7. A method for medical x-ray diagnostic imaging which comprises administering to the body of a test subject an effective contrast producing amount of the x-ray contrast composition of claim 6 and subsequently obtaining an x-ray image of said test subject.

* * * * *

UNITED STATES PATENT AND TRADEMARK OFFICE
CERTIFICATE OF CORRECTION

PATENT NO. : 5,330,739
DATED : July 19, 1994
INVENTOR(S) : Carl Illig

It is certified that error appears in the above-identified patent and that said Letters Patent is hereby corrected as shown below:

In column 8, claim 1, lines 10-14, delete

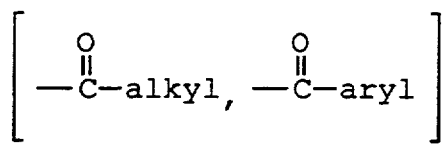

.

Signed and Sealed this

Tenth Day of January, 1995

BRUCE LEHMAN

*Attest:*

*Attesting Officer*   *Commissioner of Patents and Trademarks*